(12) United States Patent
Uber, III et al.

(10) Patent No.: US 10,378,949 B2
(45) Date of Patent: Aug. 13, 2019

(54) SYRINGE WITH INDICATOR FLOAT

(71) Applicant: BAYER HEALTHCARE LLC, Whippany, NJ (US)

(72) Inventors: Arthur E. Uber, III, Pittsburgh, PA (US); Kevin P. Cowan, Allison Park, PA (US); Stephen Sams, Bassingbourn (GB)

(73) Assignee: Bayer HealthCare LLC, Whippany, NJ (US)

( * ) Notice: Subject to any disclaimer, the term of this patent is extended or adjusted under 35 U.S.C. 154(b) by 210 days.

(21) Appl. No.: 15/317,167

(22) PCT Filed: Jun. 9, 2015

(86) PCT No.: PCT/US2015/034873
§ 371 (c)(1),
(2) Date: Dec. 8, 2016

(87) PCT Pub. No.: WO2015/191560
PCT Pub. Date: Dec. 17, 2015

(65) Prior Publication Data
US 2017/0115156 A1    Apr. 27, 2017

Related U.S. Application Data

(63) Continuation of application No. 62/010,160, filed on Jun. 10, 2014.

(51) Int. Cl.
*G01F 23/76* (2006.01)
*G01F 23/64* (2006.01)
(Continued)

(52) U.S. Cl.
CPC ......... *G01F 23/76* (2013.01); *A61M 5/14546* (2013.01); *A61M 5/31511* (2013.01);
(Continued)

(58) Field of Classification Search
CPC .. A61M 5/1685; A61M 5/16845; A61M 5/40; A61M 2205/3379;
(Continued)

(56) References Cited

U.S. PATENT DOCUMENTS 3,227,173 A * 1/1966 Bernstein ............... A61M 5/40
128/114.1
3,597,973 A * 8/1971 Ryder ................. G01F 23/2922
73/291

(Continued)

FOREIGN PATENT DOCUMENTS

DE   4319115 A1   12/1994
EP   0755691 A1   1/1997
(Continued)

OTHER PUBLICATIONS

Comar., "Oral Syringes", Jul. 2015.
(Continued)

*Primary Examiner* — Bradley J Osinski
*Assistant Examiner* — Nilay J Shah
(74) *Attorney, Agent, or Firm* — Joseph L. Kent; David Schramm; James R. Stevenson (57) ABSTRACT

A syringe assembly may include a syringe having a distal end, a proximal end, and a sidewall extending between the distal end and the proximal end and defining an interior volume; and an indicator float provided in the interior volume of the syringe. The indicator float may be buoyant such that the indicator float is movable between the distal end and the proximal end of the syringe based on a fluid fill level within the interior volume of the syringe.

12 Claims, 10 Drawing Sheets

(51) Int. Cl.
*A61M 5/145* (2006.01)
*A61M 5/40* (2006.01)
*A61M 5/315* (2006.01)
*G01F 11/02* (2006.01)
*A61M 5/00* (2006.01)

(52) U.S. Cl.
CPC ............. *A61M 5/40* (2013.01); *G01F 23/64* (2013.01); *A61M 5/007* (2013.01); *A61M 2205/583* (2013.01); *G01F 11/027* (2013.01)

(58) Field of Classification Search
CPC .. A61M 2205/3382; A61M 2205/3386; A61M 2205/3389; G01F 23/30; G01F 23/76
See application file for complete search history.

(56) References Cited

U.S. PATENT DOCUMENTS

| | | | |
|---|---|---|---|
| 4,384,581 A * | 5/1983 | Conway | A61M 5/31531 600/584 |
| 4,452,251 A | 6/1984 | Heilman | |
| 5,000,735 A | 3/1991 | Whelan | |
| 5,254,101 A | 10/1993 | Trombley, III | |
| 5,383,858 A | 1/1995 | Reilly et al. | |
| 5,868,715 A | 2/1999 | Tung | |
| 5,873,861 A | 2/1999 | Hitchins et al. | |
| 6,322,535 B1 | 11/2001 | Hitchins et al. | |
| 6,652,489 B2 | 11/2003 | Trocki | |
| 7,553,294 B2 | 6/2009 | Lazzaro et al. | |
| 7,666,169 B2 | 2/2010 | Cowan et al. | |
| 8,173,995 B2 | 5/2012 | Ramakrishnan et al. | |
| 8,403,909 B2 | 3/2013 | Spohn et al. | |
| 9,173,995 B1 | 11/2015 | Tucker et al. | |
| 9,199,033 B1 | 12/2015 | Cowan et al. | |
| 9,474,857 B2 | 10/2016 | Riley et al. | |
| 2008/0105257 A1 * | 5/2008 | Klasek | A61M 16/0875 128/203.27 |
| 2011/0056290 A1 | 3/2011 | Bryant et al. | |
| 2011/0208350 A1 | 8/2011 | Eliuk et al. | |
| 2011/0218501 A1 * | 9/2011 | Wang | 604/254 |
| 2012/0127290 A1 | 5/2012 | Tojo et al. | |
| 2012/0296288 A1 | 11/2012 | Wang | |
| 2015/0003741 A1 | 1/2015 | Zhang et al. | |
| 2015/0125945 A1 | 5/2015 | Holmes et al. | |

FOREIGN PATENT DOCUMENTS

| | | | |
|---|---|---|---|
| GB | 2147087 A * | 5/1985 | .......... A61M 5/1411 |
| WO | 2004064904 A1 | 8/2004 | |
| WO | 2012155035 A1 | 11/2012 | |
| WO | 2015081109 A1 | 6/2015 | |
| WO | 2015116637 A2 | 8/2015 | |
| WO | 2015164783 A1 | 10/2015 | |
| WO | 2016069711 A1 | 5/2016 | |
| WO | 2016069714 A1 | 5/2016 | |

OTHER PUBLICATIONS

"International Search Report and Written Opinion from corresponding PCT App. No. PCT/US2016/048441", dated Dec. 7, 2016.
Sidam; Medical Devices., "Injector Syringe With Automatic Three-Way Valve (received Jul. 9, 2014)".
"Partial Supplementary European Search Report in EP Application No. 15807247", dated Jan. 22, 2018.
Extended Search Report from EP App. No. 15807247 dated May 23, 2018.
"International Preliminary Report on Patentability from PCT Application No. PCT/US2015/034873", dated Dec. 22, 2016.
"International Search Report from PCT/US2015/034873", dated Sep. 4, 2015.

* cited by examiner

SYRINGE WITH INDICATOR FLOAT

CROSS REFERENCE TO RELATED APPLICATION

This application is a U.S. national stage filing under 35 U.S.C. § 371 of International Application No. PCT/US2015/034873, filed Jun. 9, 2015, which claims the benefit of U.S. Provisional Patent Application No. 62/010,160, filed Jun. 10, 2014, the disclosure of which is incorporated in its entirety by reference.

BACKGROUND OF THE INVENTION

Field of the Invention

The present disclosure relates to the medical field and, more particularly, to a syringe for use in the medical field where the syringe includes an indicator float configured to visually indicate a presence of a fluid inside the syringe.

Description of Related Art

A number of injector-actuated syringes and powered injectors for use in medical procedures have been developed. Typically, such injectors have drive members, such as pistons, that connect to a syringe plunger. The syringe generally includes a barrel with the syringe plunger being slidably disposed within the barrel. The drive members are configured for driving the plungers in a proximal and/or distal direction relative to a longitudinal axis of the barrel to aspirate a fluid into the syringe barrel or deliver the fluid from the syringe barrel. Current fluid delivery systems that utilize at least two syringes often contain different types of medical fluid in each syringe, such as contrast provided in one syringe and saline provided in a separate syringe. Because most injected fluids are clear, it is important to ensure that there is liquid in the syringe rather than gas and preferably to properly identify the fluid to ensure that the proper fluid is being administered to a patient.

Although substantial advances have been made in the design of syringes, it remains desirable to develop improved designs of syringes to facilitate injection procedures and fluid identification methods.

SUMMARY OF THE INVENTION

The present disclosure generally relates to syringe assemblies and to methods of identifying fluids contained in syringe assemblies.

In one aspect, a syringe assembly is disclosed. The syringe assembly may include a syringe having a distal end, a proximal end, and a sidewall extending between the distal end and the proximal end and defining an interior volume; and an indicator float provided in the interior volume of the syringe. The indicator float may be buoyant such that the indicator float is movable between the distal end and the proximal end of the syringe based on a fluid fill level within the interior volume of the syringe.

The indicator float may include a cap, a base, and at least one arm connecting the base to the cap. The at least one arm may extend radially and longitudinally in a distal direction from the base to the cap. The indicator float may have a frusto-conical shape. A plunger may be provided in the interior volume of the syringe. The plunger may be movable between the distal end and the proximal end of the syringe. The plunger may have a shape that substantially corresponds to a shape of the indicator float. The indicator float may have at least one opening between at least two arms. The cap may have an annular shape with a central opening. The base may have an annular shape with a central opening. The base may define a plurality of openings. The openings defined by the base may be circumferentially spaced around the base. A movably captured member may be provided on the indicator float. A captured member enclosure may be provided on the indicator float. The captured member enclosure may be configured to retain the captured member such that the captured member is movable within the captured member enclosure. The captured member may float in some fluids and not in others, depending upon the density of the fluid. An outer circumferential surface of the indicator float may be sized to be in proximity to the sidewall. At least two lower arms may extend in a proximal direction from the base to a lower cap. The at least two arms may spiral from the base to the cap. The indicator float may be sized and positioned in the interior volume of the syringe to prevent pivoting of the indicator float relative to the longitudinal axis of the syringe. A second indicator float may be positioned in the interior volume of the syringe. Each indicator float may have a different density and/or buoyancy.

In another aspect, an indicator float for a syringe is disclosed. The indicator float may include a cap, a base, and at least two arms connecting the base to the cap. The at least two arms may extend radially and longitudinally in a distal direction from the base to the cap. The indicator float may be buoyant and configured to indicate a presence of a fluid stored in a syringe by floating on a surface of the fluid.

The indicator float may have a frusto-conical shape. The base may define a plurality of openings. The openings defined by the base may be circumferentially spaced around the base. A movably captured member may be provided on the indicator float. A captured member enclosure may be provided on the indicator float. The captured member enclosure may be configured to retain the captured member such that the captured member is movable within the captured member enclosure. An outer circumferential surface of the indicator float may be sized in proximity to a sidewall of a syringe. At least two lower arms may extend in a proximal direction from the base to a lower cap. The at least two arms may spiral from the base to the cap.

In another aspect, a fluid delivery system is disclosed. The fluid delivery system may include a fluid injector comprising at least one piston, at least one syringe provided on the fluid injector, and an indicator float provided within the interior volume of the at least one syringe. The at least one syringe may have a distal end, a proximal end, and a sidewall extending from the distal end to the proximal end. The sidewall may define an interior volume. The indicator float may be buoyant such that the indicator float is movable between the distal end and the proximal end of the syringe based on a fluid fill level within the interior volume of the syringe. A plunger may be provided in the interior volume of the at least one syringe. A shape of the plunger may substantially correspond to a shape of the indicator float.

Further details and advantages of various aspects described in detail herein will become clear upon reviewing the following detailed description of the various aspects in conjunction with the accompanying figures.

DESCRIPTION OF THE DISCLOSURE

The illustrations generally show preferred and non-limiting aspects of the systems and methods of the present disclosure. While the descriptions present various aspects of the devices, it should not be interpreted in any way as limiting the disclosure. Furthermore, modifications, concepts, and applications of the disclosure's aspects are to be interpreted by those skilled in the art as being encompassed, but not limited to, the illustrations and descriptions provided herein.

The following description is provided to enable those skilled in the art to make and use the described aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

Further, for purposes of the description hereinafter, the terms "end", "upper", "lower", "right", "left", "vertical", "horizontal", "top", "bottom", "lateral", "longitudinal", and derivatives thereof shall relate to the disclosure as it is oriented in the figures. The term "proximal" refers to the direction in which fluid flows when entering the syringe tip or port. The term "distal" refers to the direction in which fluid flows when leaving the syringe tip or port. Up and down are used with respect to the direction of gravity. However, it is to be understood that the disclosure may assume various alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting. For the purpose of facilitating understanding of the disclosure, the accompanying drawings and description illustrate preferred aspects thereof, from which the disclosure, various aspects of its structures, construction and method of operation, and many advantages may be understood and appreciated.

Figure 1:
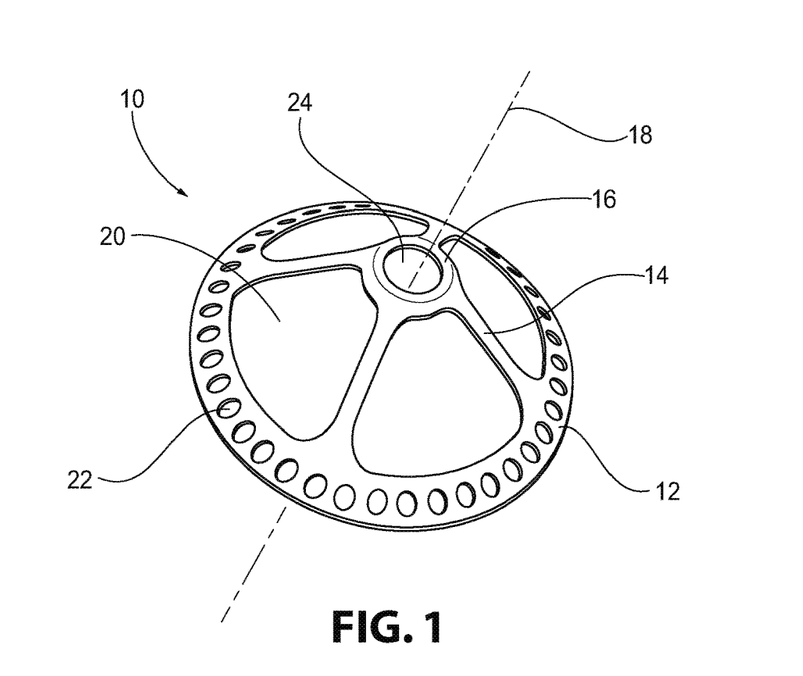
FIG. 1 is a top perspective view of an indicator float for a syringe assembly according to one aspect of the disclosure.

FIG. 1 illustrates an aspect of an indicator float 10 adapted to interface with a syringe of a fluid delivery system (shown in FIG. 4) which may be fluidly connected to a source of first fluid (not shown) or a source of second fluid (not shown), where the first and second fluids may be any desired medical fluids, such as saline, contrast, drugs, cell cultures, etc. In one aspect, the indicator float 10 may include a base 12 and a plurality of radial arms 14 extending from the base 12 and connected to a cap 16. In one aspect, the base 12, the plurality of arms 14, and the cap 16 are molded as a single, unitary piece. The indicator float 10 may be molded using a polypropylene or polyethylene material. It is also contemplated, however, that alternative materials may be used to mold the indicator float 10. In one aspect, the indicator float 10 may be compressible. In one aspect, the indicator float 10 is frusto-conical. The diameter of the indicator float 10 may decrease from the base 12 to the cap 16. In one aspect, the indicator float 10 may have a circular cross-sectional shape. It is to be understood, however, that alternative shapes for the cross-section of the indicator float 10 are contemplated, such as polygonal, including trapezoidal, toroidal, triangular, hexagonal, or oval-shaped, among others. The cross-sectional shape of the indicator float 10 may correspond to a cross-sectional shape of a syringe. The base 12 and the cap 16 may each have an annular shape with a central opening defined therein.

Figure 2:
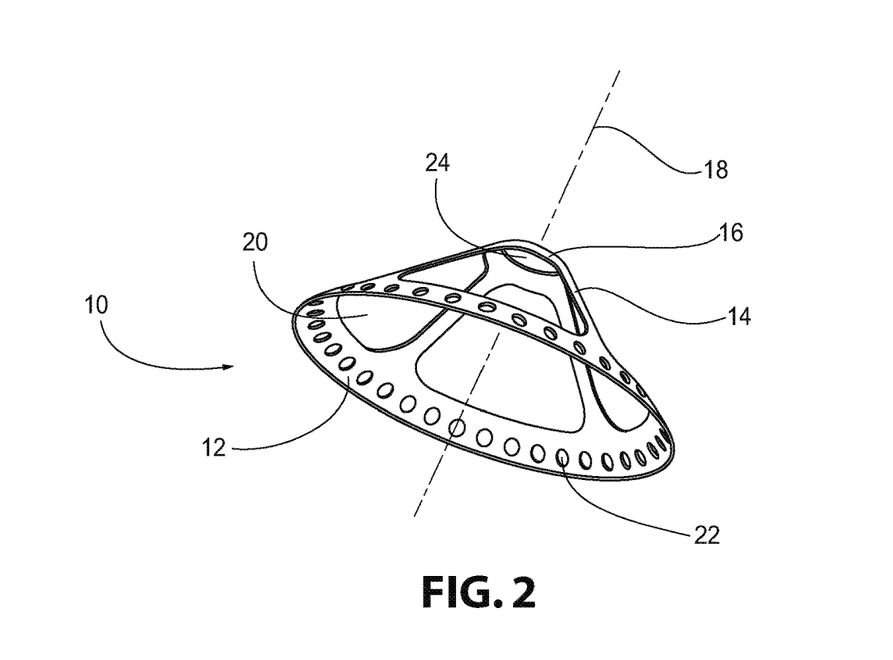
FIG. 2 is a bottom perspective view of the indicator float of FIG. 1.

The arms 14 may extend radially and/or longitudinally from the base 12 to the cap 16. In one aspect, the arms 14 are positioned at an angle relative to a longitudinal central axis 18 of the indicator float 10, thereby creating the frusto-conical shape of the indicator float 10. In one aspect, the cap 16 may be provided at a different height from the base 12, such that the cap 16 is extended away from the base 12. As shown in FIGS. 1 and 2, in one aspect, the arms 14 may be spaced evenly apart with respect to one another. It is to be understood, however, that different radial configurations of the arms 14 are contemplated. It is also to be understood that, although four arms 14 are shown in FIGS. 1 and 2, more or fewer arms may be provided with the indicator float 10. A plurality of openings 20 may be defined between the arms 14 of the indicator float 10. In one aspect, the openings 20 may be generally trapezoidal-shaped. However, it is to be understood that alternative shapes for the openings 20 are contemplated, such as circular, oval, and triangular, among others.

In one aspect, the base 12 has a plurality of openings 22 circumferentially spaced apart from one another. The base 12 may have one opening 22 or a plurality of openings 22. The openings 22 may be circular. However, alternative shapes are also contemplated. The openings 22 may be absent or evenly or unevenly spaced apart with respect to one another in the base 12. In one aspect, the cap 16 also defines an end opening 24 therethrough. The opening 24 may be defined in the cap 16 at a perpendicular orientation relative to the longitudinal axis 18 of the indicator float 10. The opening 24 may be circular. However, additional shapes are contemplated, such as oval, triangular, and trapezoidal. All of the openings 20-24 may be configured to permit fluid to pass through the indicator float 10, thereby allowing the indicator float 10 to move through the fluid in the syringe.

Figure 3A:
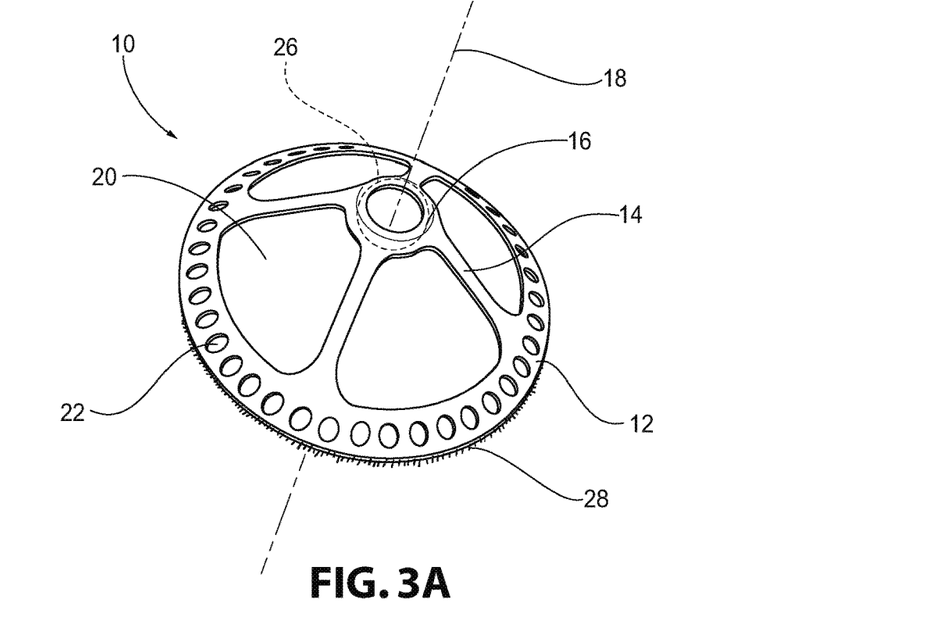
FIG. 3A is a top perspective view of an indicator float for a syringe assembly according to another aspect of the disclosure.
Figure 3B:
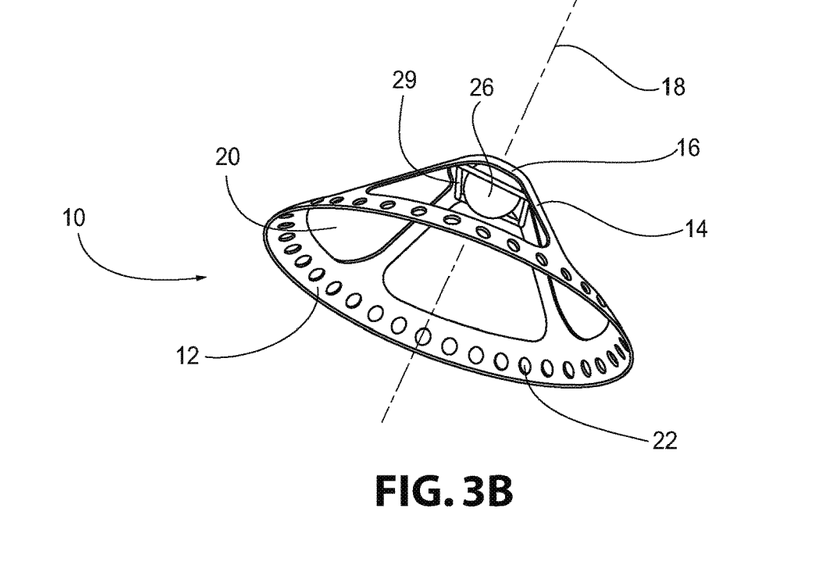
FIG. 3B is a bottom perspective view of an indicator float for a syringe assembly according to another aspect of the disclosure.
Figure 3C:
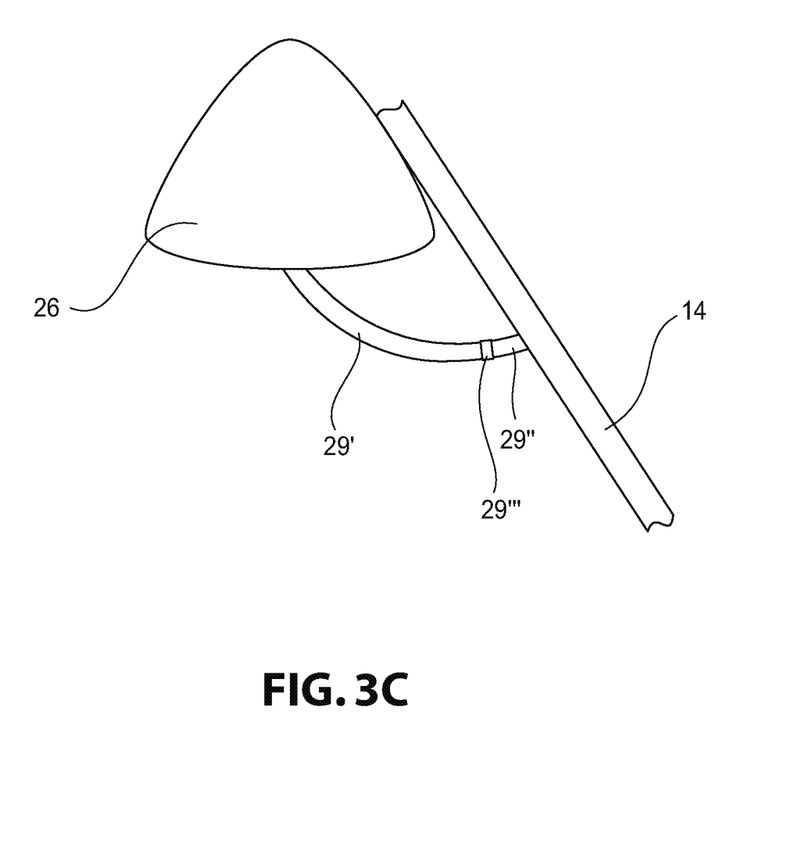
FIG. 3C is a front view of an indicator float for a syringe assembly according to another aspect of the disclosure.

As shown in FIGS. 3A-3C, an alternate aspect of the indicator float 10 is described. This alternate aspect includes the same features of the indicator float 10 shown in FIG. 1, but further includes a movable captured member 26 positioned in the end opening 24 defined by the cap 16 or on a bottom surface of the cap 16. The captured member 26 is preferably movably held in a cage formed of one or more arms 29, as seen in FIG. 3B, which holds the captured member 26 in close proximity to end opening 24. In one position, the captured member 26 may close off opening 24. In one aspect, the captured member 26 may be a ball. The captured member 26 may be press-fit into the cap 16 or the cage 29. Alternatively, the captured member 26 may be attached to the cap 16 during the molding of the indicator float 10 or through the use of a method that attaches the captured member 26 to an inner surface of the cap 16. For example, FIG. 3C shows the captured member 26 as a cone, attached via a moving arm 29' and hinge 29''' with arm 29'' permanently attached to arm 14. The captured member 26 may also be placed on or in the cap 16 via an interference fit. The captured member 26 may be made from a material that is buoyant and light enough to rise upward through a medical fluid. Alternatively, the captured member 26 may be heavy enough to sink in the medical fluid. The captured member 26 may be spherical in shape, but alternative shapes will be readily apparent to those of skill in the art. A captured member 26 that floats in contrast but not in saline, for example a captured member with a density slightly greater than 1 gm/ml, may be used to indicate whether the fluid in the syringe 104a, 104b is contrast or saline. The captured member 26 may seal the outlet of the syringe 104a, 104b when the captured member 26 and the indicator float 10 are in the most distal position, for example in the condition when the syringe 104a, 104b is tip down and full of a gas. Alternatively, the captured member 26 may not seal the outlet in any position, for example if the captured member 26 is used to indicate fluid density. As further shown in FIG. 3A, a flexible or fine-bristled texture or material 28 may be provided on an outer circumferential surface of the base 12 of the indicator float 10. The material 28 may be provided around the entire outer circumferential surface of the base 12. Alternatively, the material 28 may be provided in separate sections around the outer circumferential surface of the base 12. The material 28 may include a rough and/or raised surface. The material 28 may be configured to dislodge or displace any micro-bubbles that develop on an inner surface of the syringe 104a, 104b. The material 28 may brush against the inner surface of the syringe 104a, 104b as the indicator float 10 moves through an interior volume 120 of the syringe 104a, 104b to dislodge the micro-bubbles, thereby preventing the injection of the micro-bubbles into a patient.

Figure 4:
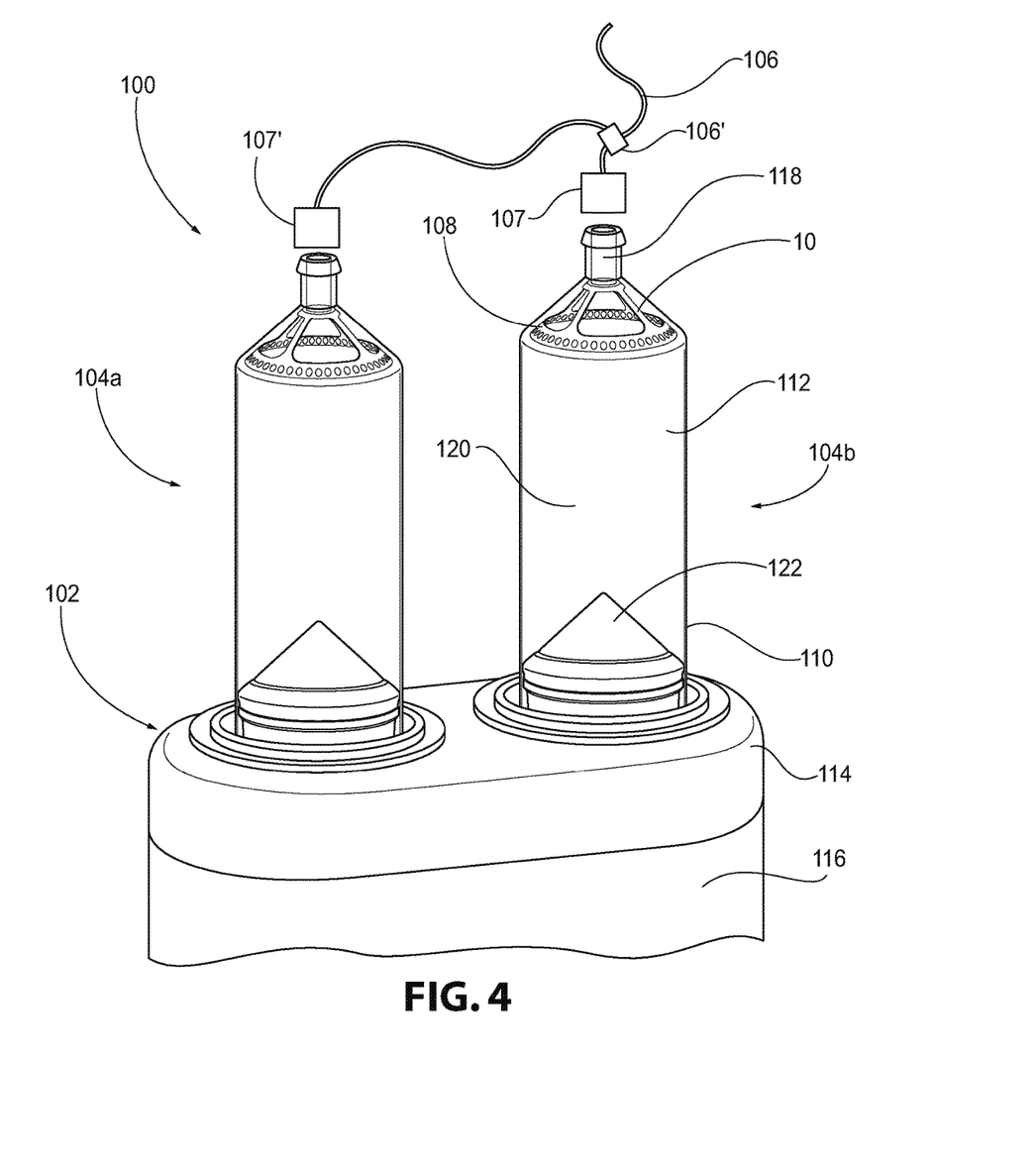
FIG. 4 is a perspective view of a fluid delivery system using the indicator float shown in FIG. 1.

As shown in FIG. 4, an indicator float 10 may be adapted to interface with a syringe 104a, 104b of an exemplary fluid delivery system 100. In one aspect, the fluid delivery system 100 may include a powered fluid injector 102. The injector 102 is desirably at least a dual-syringe injector, wherein two fluid delivery syringes 104a, 104b are oriented in a side-by-side relationship and which are separately actuated by respective piston elements (not shown) associated with the injector 102.

The injector 102 may be operatively associated with a fluid control module (not shown) which is generally adapted to support a fluid path set 106 configured to fluidly connect to the first and second syringes 104a, 104b to either supply fluid to the first and second syringes 104a, 104b or deliver fluid from the first and second syringes 104a, 104b. Each syringe 104a, 104b may have its own, separate fluid path to the patient. Alternatively, a single line to the patient may have two connectors 107 and 107' that may be connected to the two syringes 104a, 104b. The line may be in the shape of a T or Y to form a single output or outlet tube via a junction or active or passive valve 106'. The first and second syringes 104a, 104b may have the same or different sizes relative to one another. For example, one of the first syringe 104a and the second syringe 104b may be larger relative to the other of the first syringe 104a and the second syringe 104b to receive a larger volume of fluid therein. The flow of the first injection to and from the first syringe 104a and the second injection to and from the second syringe 104b is regulated by the fluid control module, which controls the various motors for syringes 104a and 104b and/or other valves and flow regulating structures to regulate the delivery of first and second fluids to the patient based on user selected injection parameters, such as total injection volume and ratio of contrast solution to saline. The fluid path set 106 may further connect to a catheter (not shown) which is associated with the patient for delivering the first and second fluids to the patient.

The syringe 104a, 104b may be a unitary, typically cylindrical, body having a distal end 108 and a proximal end 110 and may be a reusable component. In another aspect, the syringe 104a, 104b may be a single-use component that is disposed after each patient use. In this aspect, the syringe 104a, 104b is disposed of after each use and a new syringe 104a, 104b is loaded into the fluid injector 102. The syringe 104a, 104b has a sidewall 112 that extends between and defines a cavity between the distal and proximal ends 108, 110. The proximal end 110 is adapted to interface with the fluid injector 102 and may include a mounting structure (not shown) positioned to engage the front end or face plate 114 of the housing 116 of the fluid injector 102 to properly seat the syringe 104a, 104b relative to the fluid injector 102. As an example, two opposed bayonet attachment flanges (not shown) may be provided on the proximal end 110 for interfacing with a fluid injector face plate 114 to secure the syringe 104a, 104b to the fluid injector 102. The distal end 108 of the syringe 104a, 104b may include a substantially frusto-conical portion that terminates in a port 118. The syringe 104a, 104b may be made of any suitable plastic material, desirably a clear plastic material, such as, but not limited to, polycarbonate, acrylic, or polyester.

With continuing reference to FIG. 4, the syringe 104a, 104b defines an interior volume 120. The proximal end 110 of the syringe 104a, 104b may be shaped to interface directly with a plunger 122 connected to a piston (not shown) of the fluid injector 102. The port 118 may have, according to one non-limiting aspect, a fracturable seal for sterility purposes, such as piercable foil or an elastomeric seal. The indicator float 10 may be positioned within the interior volume 120 of the syringe 104a, 104b. The frusto-conical shape of the indicator float 10 may correspond to the frusto-conical shape of the distal end 108 of the syringe 104a, 104b and the frusto-conical shape of the plunger 122. In this aspect, the cap 16 of the indicator float 10 may be positioned closer to the distal end 108 of the syringe 104a, 104b and the base 12 of the indicator float 10 may be positioned closer to the proximal end 110 of the syringe 104a, 104b such that a residual volume of fluid remaining in the syringe 104a, 104b is reduced or eliminated when the plunger 122 is at the distal end 108. The indicator float 10 is freely-movable within the syringe 104a, 104b between the distal end 108 and the proximal end 110. The frusto-conical shape of the indicator float 10 may assist in preventing turbulence in the fluid as the fluid is filled in the syringe 104a, 104b. As the fluid is supplied into the syringe 104a, 104b, the fluid contacts the cap 16 of the indicator float 10 and at least a portion of the fluid may be directed down the arms 14 of the indicator float 10. The fluid may then be directed against the inner surface of the syringe 104a, 104b, which creates a less turbulent flow into the syringe 104a, 104 than if the fluid was directed downwards to contact the plunger 122 of the syringe 104a, 104b. The indicator float 10 may be shaped and positioned in the interior volume 120 of the syringe 104a, 104b to permit rotation of the indicator float 10 around a longitudinal axis of the syringe 104a, 104b and prevent pivoting of the indicator float 10 relative to the longitudinal axis of the syringe 104a, 104b to ensure that the indicator float 10 remains properly positioned in the syringe 104a, 104b.

Figure 8:
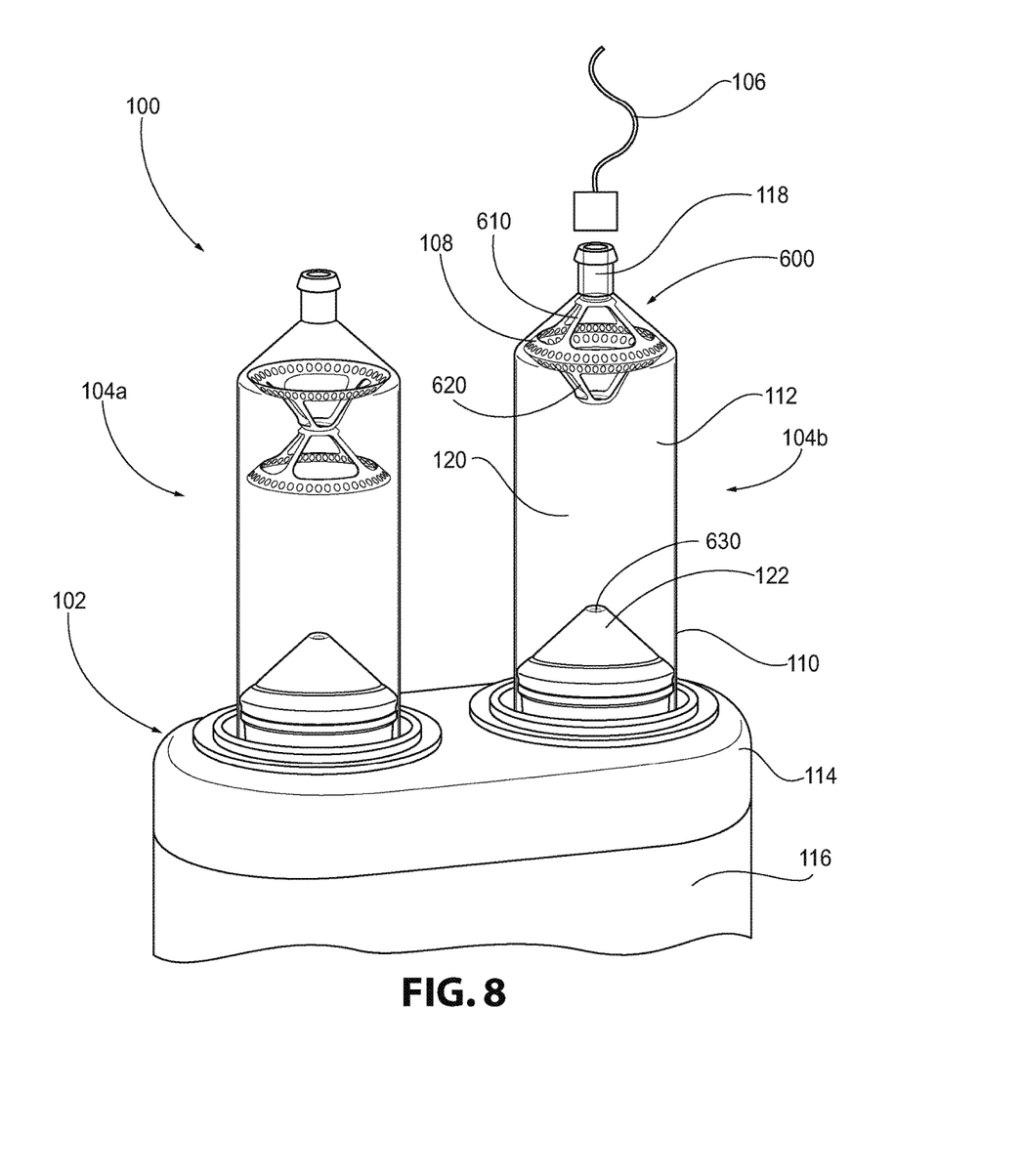
FIG. 8 is a perspective view of a fluid delivery system using an indicator float according to another aspect of the present disclosure.

As seen in FIG. 4, at least one syringe 104a, 104b may include an indicator float 10 therein. The indicator float 10 is configured to float within the syringe 104a, 104b as the syringe 104a, 104b is filled with a medical fluid, such as contrast or saline. As the syringe 104a, 104b is filled, the indicator float 10 provides a visual identification of the fill level of the syringe 104a, 104b. Before filling the syringes 104a, 104b with medical fluids, such as when the syringe 104a, 104b are empty, the indicator float 10 may rest on the plunger 122 of the syringe 104a, 104b. As each syringe 104a, 104b is filled with fluid, the indicator float 10 begins to rise or float in the liquid from the proximal end 110 to the distal end 108 of the syringe 104a, 104b. In one aspect, where the first syringe 104a may be filled with contrast and the second syringe 104b may be filled with saline, the indicator float 10 is used to identify which syringe 104a, 104b is filled with which medical fluid. For example, since the contrast of the first syringe 104a has a higher viscosity than the saline of the second syringe 104b, the indicator float 10 in the first syringe 104a will float toward the distal end 108 more slowly than the indicator float 10 in the second syringe 104b when the syringe 104b is inverted such that the distal end 108 is pointed downward relative to the proximal end 110. Based on a speed in which the indicator float 10 moves through the fluid, the user may be able to identify the type of fluid provided in the syringe 104a, 104b. The rate that the indicator float 10 rises towards the proximal end 110 of the syringe 104a, 104b is correlative to the viscosity of the fluid contained in the syringe 104a, 104b. Since the contrast has a higher viscosity than the saline, the indicator float 10 will move more slowly through the contrast than through the saline. Therefore, the user can easily identify which syringe 104a, 104b contains which medical fluid. In an alternative embodiment, as shown in FIG. 8, each syringe 104a, 104b has a distal indicator float 610 and a more proximal indicator float, 620, either identical or different. The distal indicator float 610 may have a density such that it floats in any liquid which is likely to be placed in the syringe 104a, 104b. For example, water and saline have a density of about 1 gm/ml. X-ray and MR contrast can have a density approaching 1.3 gm/ml, depending upon concentration. For use with such fluids, the distal indicator float 610 may have a density less than 1 gm/ml, for example of polyethylene or polypropylene which can have a density of 0.9 gm/ml. The second, more proximal indicator float 620 may be made to have a density a little greater than saline, for example 1.1 gm/ml. Nylon is one material that can be used. A second alternative is to include additional materials, for example inert fillers, in the plastic to increase its density to the desired level. A third alternative is to choose a dense plastic and to use trapped air or less dense material to decrease its density. In operation, if the syringe 104a, 104b, pointed up as shown in FIG. 8, is filled with saline, the distal indicator float 610 rises with the fluid level, but the more proximal and denser indicator float 620 would not rise. If the syringe 104a, 104b is filled with contrast of sufficient density, then both the distal indicator float 610 and the more proximal indicator float 620 rise in the liquid.

The indicator float 10 also assists in collecting or dislodging small or micro-bubbles that develop on an inner surface of the sidewall 112 of the syringe 104a, 104b as the syringe 104a, 104b is filled with medical fluid. As medical fluid is injected into and/or out of the syringe 104a, 104b, micro-bubbles may develop on the inner surface of the sidewall 112 of the syringe 104a, 104b due to turbulence created in the medical fluid, for example at the air-liquid interface. In one aspect, an outer surface of the base 12 of the indicator float 10 may contact the inner surface of the sidewall 112 of the syringe 104a, 104b so, as the micro-bubbles develop on the sidewall 112, the base 12 of the indicator float 10 dislodges or collects the micro-bubbles as the indicator float 10 rises in the fluid, for example towards the distal end 108 of the syringe 104a, 104b if the port 118 is up, or towards the proximal end 110 if the port 118 is down. The operator may rotate the injector head from the position with the port 118 up to that with port 118 down to dislodge bubbles, and if the bubbles are significant enough, optionally to the position with the port 118 up for removal of the accumulated gas. This can be repeated if necessary. By dislodging or collecting the micro-bubbles, the indicator float 10 assists in directing the micro-bubbles to the distal end 108 of the syringe 104a, 104b. With the micro-bubbles collected at the distal end 108 and port 118 of the syringe 104a, 104b, the priming of the syringe 104a, 104b may be done more quickly and more efficiently, enabling the micro bubbles to be discharged from the syringe 104a, 104b during priming. In one aspect, the flexible or fine-bristled texture or material 28 may be provided on the outer circumferential surface of the base 12 to provide additional assistance in removing the micro-bubbles from the sidewall 112 of the syringe 104a, 104b. When using the flexible or fine-bristled texture or material 28, the outer diameter of the base 12 of the indicator float 10 may be smaller to accommodate the flexible or fine-bristled texture or material 28, which helps in reducing the occurrence of the indicator float 10 becoming lodged or jammed against the sidewall 112 of the syringe 104a, 104b.

When using the indicator float 10 that includes the captured member 26 (shown in FIGS. 3A and 3B), the captured member 26 may be used to seal or at least partially obstruct the port 118 of the syringe 104a, 104b when the syringe 104a, 104b is empty or partially full. As the syringe 104a, 104b is filled up with medical fluid, the indicator float 10 and the captured member 26 rise through the syringe 104a, 104b towards the port 118. Once the syringe 104a, 104b is filled, the syringe 104a, 104b is rotated so that the port 118 is directed downwardly towards a patient. As the syringe 104a, 104b is rotated, the indicator float 10 begins to float upward towards the proximal end 110 of the syringe 104a, 104b. As the medical fluid is ejected from the syringe 104a, 104b, the indicator float 10 moves downwardly towards the port 118 and the distal end 108 of the syringe 104a, 104b. Once all of the medical fluid is ejected from the syringe 104a, 104b, the captured member 26 of the indicator float 10 is plugged into or pressed against the port 118. By sealing the port 118, the injector 102 is prevented from ejecting any air out of the syringe 104a, 104b. Therefore, the indicator float 10 and the captured member 26 float on the top surface of the medical fluid as the medical fluid is ejected from the syringe 104a, 104b, until all of the medical fluid has been ejected from the syringe 104a, 104b. In turn, the captured member 26 is positioned against the port 118 to create a seal to prevent air from escaping from the syringe 104a, 104b.

Figure 5:
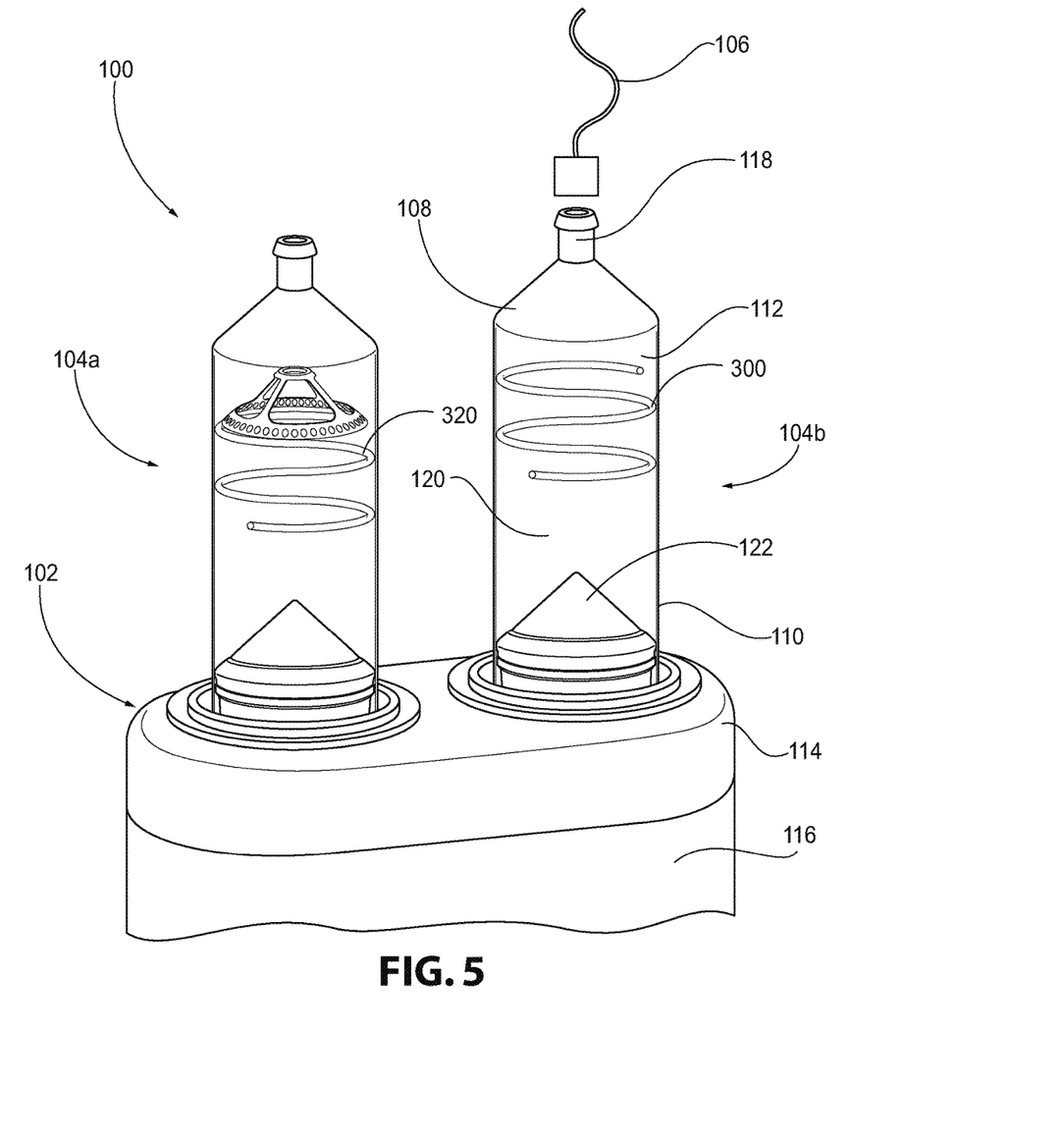
FIG. 5 is a perspective view of a fluid delivery system using an indicator float according to another aspect of the present disclosure.

With reference to FIG. 5, another aspect of an indicator float 300 is described. Similar to the indicator float 10 above, this indicator float 300 may be inserted into a syringe, for example syringe 104a, to identify characteristics of the fluid stored in the syringe 104a. The indicator float 300 may have a spiral shape, preferable with a flat, thin cross section similar to that of a Slinky® toy, in other words, a thin coiled strip, which extends along a longitudinal length of the syringe 104a. The indicator float 300 may be configured to float within the fluid stored in the syringe 104a. In one aspect, the indicator float 300 may be compressible so that, as the plunger 122 is moved towards the distal end 108 of the syringe 104a, the indicator float 300 may compress to allow the plunger 122 to dispel a maximum volume of fluid from the syringe 104a. As the plunger 122 is pulled back to the proximal end 110 of the syringe 104a, the indicator float 300 may expand back to an original position. To facilitate this, the spiral may go in one direction, for example clockwise in the distal portion of the float and counterclockwise in the proximal portion of the float. The spiral may be sized and configured to assist in removing bubbles from the inside wall of the syringe 104a. A benefit of an indicator float 300 with an axial length that contacts the sidewalls is that the indicator float 300 is restricted from tumbling as it moves in the syringe 104a. This ensures that the indicator float 300 is oriented properly for filling and delivery and improves the removal of bubbles from the inside of the syringe 104a walls. It is also contemplated that multiple indicator floats 300 may be provided in the syringe 104a, 104b. An alternative indicator float 320, may be created by incorporating the indicator float 10 of FIG. 1 onto the distal end spiral of indicator float 300, as illustrated in syringe 104b. A further aspect, not shown, incorporates one or more captured members in the indicator float 10 as well.

Figure 6:
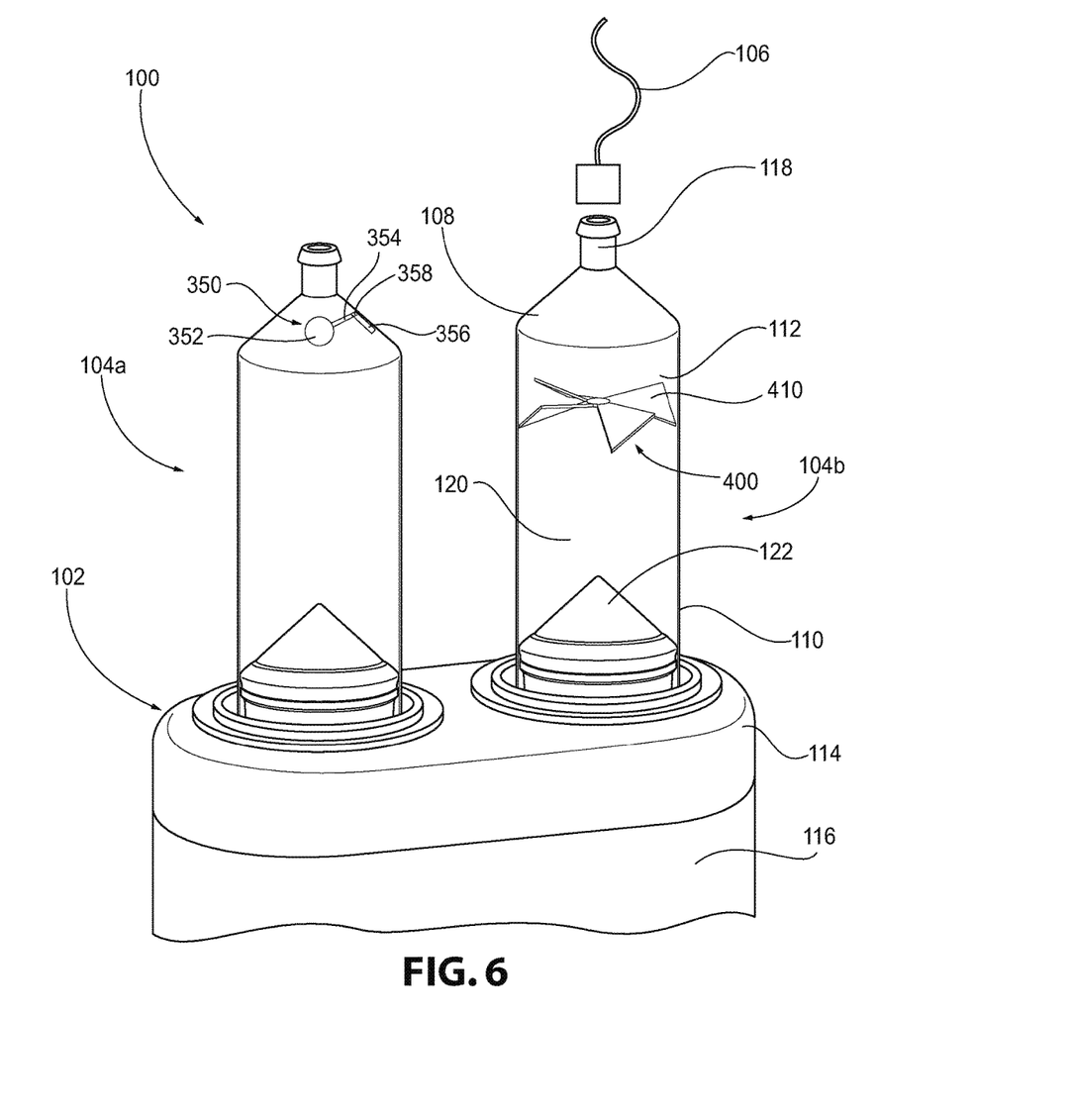
FIG. 6 is a perspective view of a fluid delivery system using an indicator float according to another aspect of the present disclosure.

With reference to FIG. 6, another aspect of an indicator float 400 is described. Similar to the indicator float 10 above, this indicator float 400 may be inserted into a syringe 104b to identify characteristics of the fluid stored in the syringe 104b. The indicator float 400 may include a fan-blade configuration. The indicator float 400 may include a plurality of blades 410 that are connected to a center portion of the indicator float 400. The blades 410 may be provided in a circular configuration around the inner circumferential surface of the syringe 104b. The indicator float 400 may be configured to float within the fluid stored in the syringe 104b. The blades 410 may assist in moving the indicator float 400 through the fluid stored in the syringe 104b. The blades 410 may be sized to assist in removing bubbles from the inside wall of the syringe 104b. The blades 410 may be angled relative to one another to create a spiral effect with the indicator float 400 which increases visibility or noticeability of the indicator float 400 movement to the operator or user. It is also contemplated that multiple indicator floats 400 may be provided in the syringe 104b. Indicator float 350 in syringe 104a illustrates an alternative embodiment in which the floating member 352 is tethered or attached to the syringe 104a through a leg 354 which is joined by a hinge 358 to an attachment member 356 that is fixedly attached to the syringe 104a. Alternatively, the leg 354 could be flexible enough that a hinge 358 and attachment member 356 are not needed. An example of such a flexible leg 354 is a filament or tube. Floating member 352, for example, may be a small cone, a flat flexible element, a hemisphere, or a ball.

Figure 7:
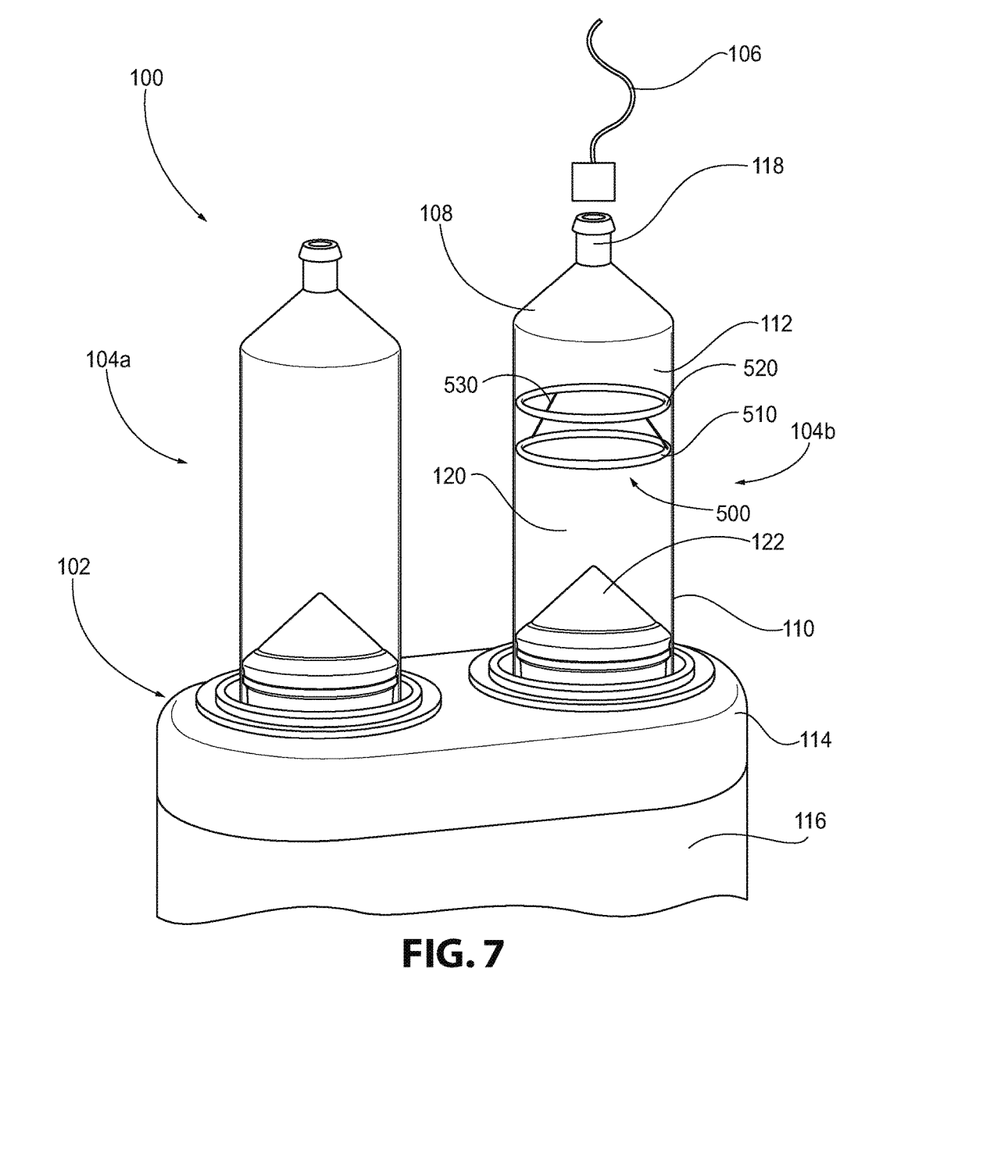
FIG. 7 is a perspective view of a fluid delivery system using an indicator float according to another aspect of the present disclosure.

With reference to FIG. 7, another aspect of an indicator float 500 is described. Similar to the indicator float 10 above, this indicator float 500 may be inserted into a syringe 104a, 104b to identify characteristics of the fluid stored in the syringe 104a, 104b. The indicator float 500 may include a lower ring 510, an upper ring 520, and support members 530 that connect the lower ring 510 and upper ring 520. The lower and upper rings 510, 520 may be circular in shape corresponding to the shape of the inner circumferential surface of the syringe 104a, 104b. The support members 530 extend between the upper ring 520 and the lower ring 510. The indicator float 500 may be integrally formed as a single unit. Alternatively, each piece of the indicator float 500 may be separately molded and connected to one another. The indicator float 500 may be compressible such that, as the plunger 122 is pushed towards the distal end 108 of the syringe 104a, 104b, the indicator float 500 compresses to allow a maximum volume of fluid to be dispelled from the syringe 104a, 104b via the plunger 122. In this aspect, the support members 530 may compress to bring the lower ring 510 and the upper ring 520 closer to one another. As the plunger 122 is pulled back towards the proximal end 110 of the syringe 104a, 104b, the indicator float 500 may expand back to an original position. By providing a sufficient longitudinal length of the indicator float 500 in proximity to the syringe 104a, 104b walls, for example in this embodiment, two rings 510, 520 in the indicator float 500, the indicator float 500 may be more stable within the syringe 104a, 104b and less prone to rotate and tip over into an undesired position. It is also contemplated that multiple indicator floats 500 may be provided in the syringe 104a, 104b.

With reference to FIG. 8, another aspect of an indicator float 600 is described. Similar to the indicator float 10 above, this indicator float 600 may be inserted into a syringe 104a, 104b to identify characteristics of the fluid stored in the syringe 104a, 104b. The indicator float 600 may have a double cone shape that includes an upper member 610 and a lower member 620. The members 610, 620 may be shaped substantially similarly to the indicator float 10 described hereinabove. The members 610, 620 may be separate or attached to one another at their respective base or tip portions. The members 610, 620 may have identical or similar densities or may have densities different enough that the indicator float 600 rotates as it moves through the syringe 104a, 104b to ensure that one end is always down. The members 610, 620 may be integrally formed with one another or connected to one another via fastening means. In one aspect, the cone tip of the upper member 610 may be directed towards the distal end 108 of the syringe 104a, 104b and the cone tip of the lower member 620 may be directed towards the proximal end 110 of the syringe 104a, 104b. The indicator float 600 may be compressible. In another aspect, the indicator float 600 may be configured to fold in on itself during an injection process. As the plunger 122 is moved towards the distal end 108 of the syringe 104a, 104b, the plunger 122 may push the cone tip of the lower member 620 inwards towards the cone tip of the upper member 610. By pushing the cone tip of the lower member 620 into the upper member 610, a maximum volume of fluid may be dispelled from the syringe 104a, 104b. It is also contemplated that captured members similar to the captured member 26 described hereinabove may be provided in the cone tip of the members 610, 620. It is also contemplated that a captured member is only provided in one of the cone tips. In one aspect, the plunger 122 may have a recessed tip 630 configured to receive a captured member provided in the cone tip of the members 610, 620. By providing the recessed tip 630, the plunger 122 may be pushed further towards the distal end 108 of the syringe 104*a*, 104*b* since the captured member is received in the recessed tip 630. Therefore, the recessed tip 630 permits a maximum volume of fluid to be dispelled from the syringe 104*a*, 104*b*. It is also contemplated that the recessed tip 630 may be provided on the plunger 122 of any fluid delivery system 100 that includes an indicator float with a captured member to maximize the amount of fluid that is dispelled from the syringe 104*a*, 104*b*. It is also contemplated that the tip of the plunger 122 may be compressible to receive the captured member 26 to maximize the volume of fluid that is dispelled from the syringe 104*a*, 104*b*.

Figure 9:
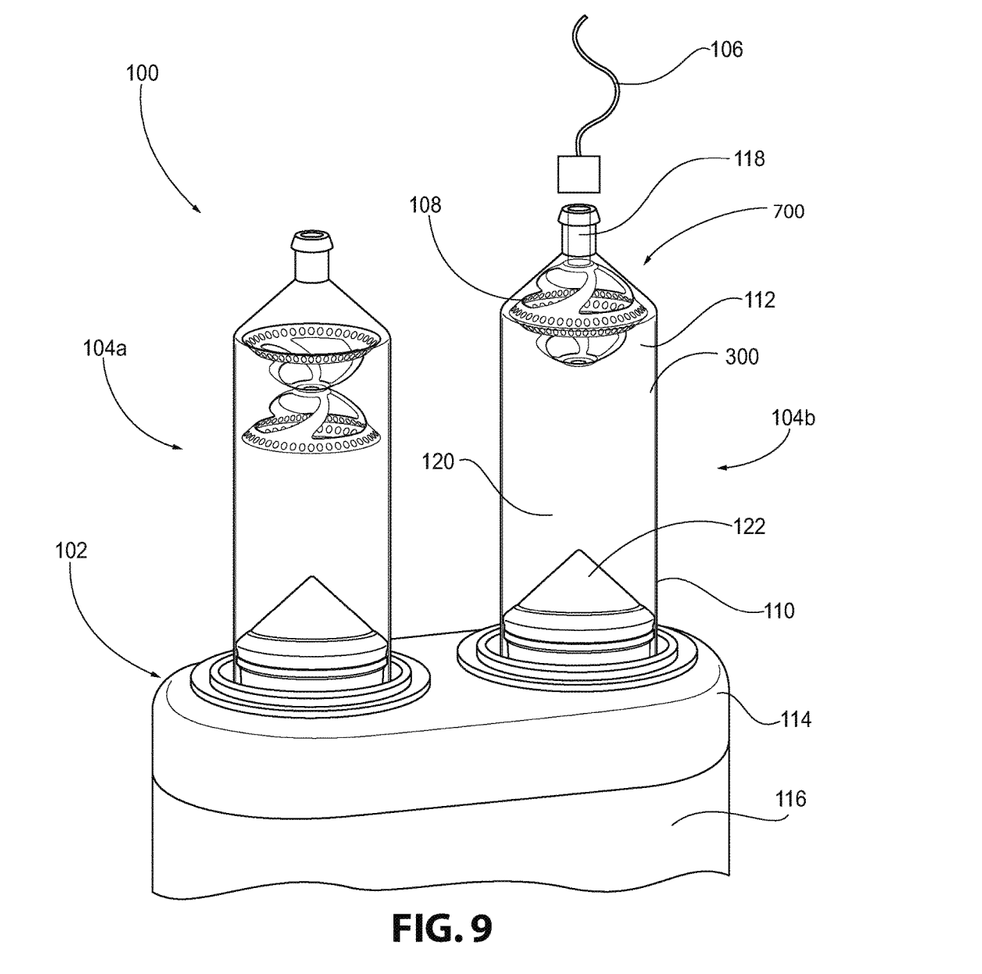
FIG. 9 is a perspective view of a fluid delivery system using an indicator float according to another aspect of the present disclosure.

With reference to FIG. 9, another aspect of an indicator float 700 is described. This indicator float 700 is similar to the indicator float 600 described in FIG. 8. However, instead of straight arm members provided on the members 610, 620 of the indicator float 600, the arms of this indicator float 700 are spiraled. The arms spiral in a circular direction from the base of each member 710, 720 to the cone tip of each member 710, 720. By providing arms that are spiraled, the indicator float 700 may be more easily folded in on itself during the injection process of the fluid delivery system 100. Further, by using the spiraled arms, the indicator float 700 may spin in one direction upon compression of the indicator float 700. Such spiral arms can be utilized in other embodiments disclosed herein, for example, as FIGS. 1-3B.

Figure 10A:
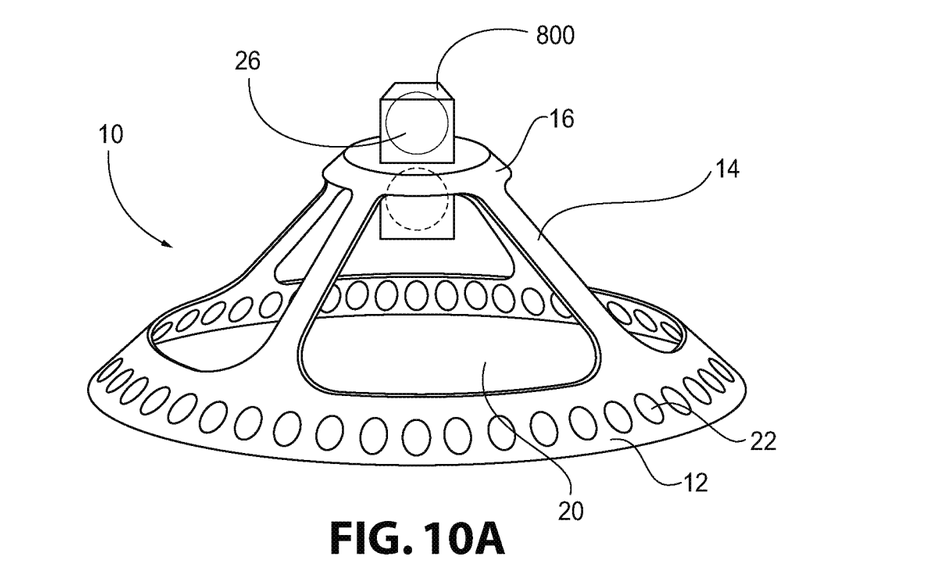
FIG. 10A is a front view of the indicator float of FIG. 1 including a captured member enclosure.
Figure 10B:
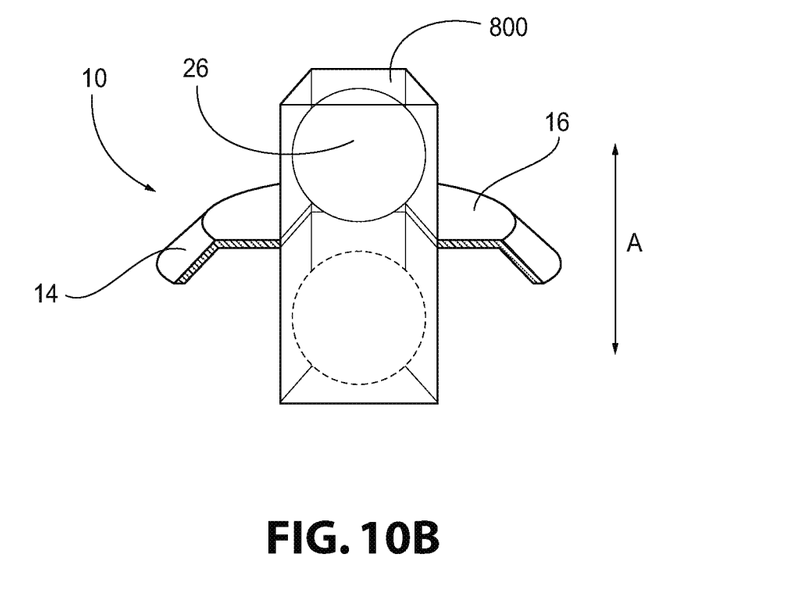
FIG. 10B is a front cross-sectional view of the indicator float of FIG. 10A.

With reference to FIGS. 10A and 10B, a captured member enclosure 800 is described. The captured member enclosure 800 may be used with any aspect of the indicator float that utilizes a captured member 26 as described above. The captured member enclosure 800 may be provided in the aperture 24 defined by the cap 16. The captured member enclosure 800 may be molded into the cap 16, adhesively connected to the cap 16, or may be provided within the cap 16 via a friction or interference fit. In one aspect, the captured member enclosure 800 is rectangular in shape. In another aspect, the captured member enclosure 800 may be square in shape. It is contemplated, however, that the captured member enclosure 800 may be formed in many alternative shapes. In this aspect, the captured member 26 may be provided within the captured member enclosure 800 and is movable between a first position and a second position. The captured member 26 may move within the captured member enclosure 800 along direction A, for example axially or optionally at an angle to the syringe axis. Using the captured member enclosure 800, when the syringe 104*a*, 104*b* is positioned with the distal end 108 in an upward direction, the captured member 26 may move to the bottom portion of the captured member enclosure 800 while the indicator float 10 moves in the liquid towards the distal end 108 of the syringe 104*a*, 104*b*. Once the distal end 108 of the syringe 104*a*, 104*b* is pointed downwards during the injection phase, the captured member 26 may move to a bottom or distal portion of the captured member enclosure 800 while the indicator float 10 moves towards the proximal end 110 of the syringe 104*a*, 104*b*. Thus liquid may be delivered. If the syringe is full of air or other gas instead of a liquid of sufficient density, then the indicator float 10 will be at the downward or distal end of the syringe 104*a*, 104*b* and the captured member 26 will be at the distal end of the captured member enclosure 800 and preferably block the port 118 of the syringe 104*a*, 104*b* so that air cannot be delivered to the patient. The indicator float 10 material must be of a density and volume to provide a net buoyancy to the indicator float 10 in the fluids being used, given that captured element 26 is more dense than the fluids being used.

The simplest indicator float described herein is buoyant in all the liquids used in the syringe so that the presence or absence of floating indicates the presence or absence of fluid. An alternative aspect described herein utilizes two indicator floats of different densities or buoyancies to give an indication of the density and thus indicate different types of liquid in the syringe, for example saline and imaging contrast. An alternative aspect of an indicator float utilizes a captured element in a float to block injection of gas when the syringe tip or port is down and yet allow in-flow of fluid and removal of air when the syringe tip is up. An alternative aspect of an indicator float has elements in proximity with the syringe sidewalls to aid in removal of bubbles that adhere to the sidewalls. An alternative aspect of an indicator float has sufficient axial length or is otherwise designed so that the indicator float cannot tumble or rotate uncontrollably in the syringe. Alternative aspects of an indicator float are thin or otherwise designed to compress so that the maximum fluid can be delivered from the syringe. The syringe plunger configuration can be selected to cooperate with the indicator float to achieve this maximum fluid efficiency. Alternative aspects of an indicator float affect, direct, or channel the inflow of the liquid as the syringe is filled to reduce the creation of air bubbles.

The indicator float of this disclosure can be a single piece made from a uniform material. For example polyethylene with a density of 0.91 to 0.96 gm/ml or polypropylene with a density of 0.57 to 0.68 gm/ml. Nylons with a density of 1.1 to 1.8 gm/ml can be used for floats that are used to distinguish different fluid densities and thus types. Fillers, either macro or micro, can be used to increase the density of the material used to create the indicator float. Less dense materials, bubbles, foams, or hollow spheres can be used to decrease the density of the material used to create the indicator float. The indicator float may be manufactured or assembled from different pieces or from different materials with different densities to provide the desired net density or buoyancy.

Example fluids with which the indicator float may be used are saline with a density of about 0.9922 at 40° C. and Visipaque with a density of 1.369 gm/ml at 20° C. and 1.356 gm/ml at 37° C.

The indicator float may include a captured member. The captured member may rise or fall in the liquids. In an aspect where the captured member is denser than all the fluids, the captured member will sink in the fluid. In an aspect in which the syringe is oriented tip down, the captured member preferably blocks the syringe port so that air cannot be delivered from the syringe.

The indicator float may generally be of a shape similar to the syringe plunger and the distal portion of the syringe to enable the delivery of the maximum volume. Alternatively, the float can be flexible, pliable or soft so that it compresses as the plunger moves against the front of the syringe to enable the delivery of the maximum volume. Alternatively, the contour of the plunger can be designed to accommodate or nest with the indicator float to enable the delivery of the maximum volume.

In use, the syringe or syringes containing an indicator float are place on an injector head and moved into position with the syringe tip (distal end of syringe) up. With no fluid in the syringe, the indicator float will be pressed against the plunger. To fill the syringe in one aspect, the plunger is first moved distally to expel air from the syringe. Then the syringe tip or port is attached to a source of fluid. The plunger is then moved proximally and fluid is pulled into the syringe by vacuum or negative pressure. The indicator float will float in the liquid and preferably interact with the fluid stream to reduce the creation of bubbles in the liquid. Once the syringe is full of the desired amount of fluid, the plunger moves distally to expel any remaining air. If there are any bubbles adhering to the side wall of the syringe, the injector head may be rotated so that the syringe tip is down. The indicator float will now move in a proximal direction dislodging air bubbles and confirming that there is fluid in the syringe. If there were no fluid in the syringe, the indicator float would move in the opposite direction so that it would fall distally in the gas. If the bubbles dislodged are of sufficient volume, the injector head may be rotated so that the syringe tip is up. The indicator float will move distally in the fluid as will the air bubbles. The air bubbles can be expelled or purged from the syringe and fluid path. The injector head is then rotated so that the syringe tips are down and indicator float is back against the plunger.

The indicator float in some aspects can tumble or rotate as it moves through the syringe. In alternative aspects, the indicator float has a heavier and a lighter aspect such that the indicator float rotates so that a specific aspect or segment of the indicator float tends to be up in relation to gravity. In alternative aspects, the indicator float rotates axially as it moves in the syringe to highlight the motion to the user and optionally to improve the removal of bubbles from the syringe sidewalls. The indicator float may be free floating within the syringe volume. In alternative aspects, the speed of rise of the indicator float is an indication of the density or type of the liquid in the syringe. It alternative aspects, the indicator float is movably attached to the plunger or the syringe such that the movement due to buoyancy is restricted to a more limited motion. This may have the advantage of preserving the orientation of the indicator float. The indicator float may have various patterns of holes, slots, legs or other arrangements of solid and absence of material including an all solid arrangement.

While aspects of an indicator float and fluid delivery system including indicator floats were provided in the foregoing description, those skilled in the art may make modifications and alterations to these aspects without departing from the scope and spirit of the disclosure. Accordingly, the foregoing description is intended to be illustrative rather than restrictive.

The invention claimed is:
1. A syringe assembly, comprising:
   a syringe having a distal end, a proximal end, and a sidewall extending between the distal end and the proximal end and defining an interior volume; and
   an indicator float provided in the interior volume of the syringe,
   wherein the indicator float comprises a cap, a base, and at least two distal arms extending radially inward and longitudinally in a distal direction from the base to the cap and connecting the cap to the base, wherein the indicator float has a frusto-conical shape, and
   wherein the indicator float is buoyant such that the indicator float is movable between the distal end and the proximal end of the syringe based on a fill level of a fluid within the interior volume of the syringe.

2. The syringe assembly of claim 1, further comprising a plunger provided in the interior volume of the syringe,
   wherein the plunger is reversibly movable between the distal end and the proximal end of the syringe; and
   wherein a distal surface of the plunger has a shape that substantially corresponds to the frusto-conical shape of the indicator float.

3. The syringe assembly of claim 1, wherein the cap has an annular shape with a central opening.

4. The syringe assembly of claim 1, wherein the base has an annular shape with a central opening.

5. The syringe assembly of claim 1, wherein the base defines a plurality of openings, wherein the plurality of openings defined by the base are circumferentially spaced around the base.

6. The syringe assembly of claim 1, further comprising a movably captured member provided on the indicator float.

7. The syringe assembly of claim 6, further comprising a captured member enclosure provided on the indicator float, wherein the captured member enclosure is configured to retain the movably captured member such that the movably captured member is movable within the captured member enclosure.

8. The syringe assembly of claim 1, wherein an outer circumferential surface of the indicator float is sized to be in proximity to the sidewall.

9. The syringe assembly of claim 1, further comprising:
   a lower cap; and
   at least two proximal arms extending in a proximal direction from the base to the lower cap.

10. The syringe assembly of claim 1, wherein the at least two distal arms connecting the base to the cap spiral from the base to the cap.

11. The syringe assembly of claim 1, wherein the indicator float is positioned in the interior volume of the syringe to prevent pivoting of the indicator float relative to a longitudinal axis of the syringe.

12. The syringe assembly of claim 1, further comprising a second indicator float positioned in the interior volume of the syringe, wherein the second indicator float has at least one of a different density and a different buoyancy than the indicator float.

* * * * *

UNITED STATES PATENT AND TRADEMARK OFFICE
CERTIFICATE OF CORRECTION

PATENT NO. : 10,378,949 B2
APPLICATION NO. : 15/317167
DATED : August 13, 2019
INVENTOR(S) : Uber, III et al.

Page 1 of 1

It is certified that error appears in the above-identified patent and that said Letters Patent is hereby corrected as shown below:

In the Specification
In Column 7, Line 8, delete "104" and insert -- 104b --, therefor.

Signed and Sealed this
Nineteenth Day of November, 2019

Andrei Iancu
*Director of the United States Patent and Trademark Office*